(12) United States Patent
Groneberg et al.

(10) Patent No.: US 7,078,425 B2
(45) Date of Patent: Jul. 18, 2006

(54) PREPARATION OF PHOSPHATASE INHIBITORS

(75) Inventors: Robert D. Groneberg, Boulder, CO (US); David A. Mareska, Longmont, CO (US)

(73) Assignee: Array Biopharma Inc., Boulder, CO (US)

( * ) Notice: Subject to any disclaimer, the term of this patent is extended or adjusted under 35 U.S.C. 154(b) by 0 days.

(21) Appl. No.: 10/512,965

(22) PCT Filed: Apr. 30, 2003

(86) PCT No.: PCT/US03/13734

§ 371 (c)(1),
(2), (4) Date: May 31, 2005

(87) PCT Pub. No.: WO03/092679

PCT Pub. Date: Nov. 13, 2003

(65) Prior Publication Data

US 2005/0256316 A1  Nov. 17, 2005

(51) Int. Cl.
  *A61K 31/405*  (2006.01)
  *A61K 31/416*  (2006.01)
  *C07D 231/56*  (2006.01)
  *C07D 209/10*  (2006.01)

(52) U.S. Cl. .................. 514/405; 514/415; 548/361.5; 548/494

(58) Field of Classification Search ............... 514/405, 514/415; 548/361.5, 494
See application file for complete search history.

(56) References Cited

FOREIGN PATENT DOCUMENTS

WO   WO 00/53583      9/2000
WO   WO 200053583 A1 * 9/2000

* cited by examiner

*Primary Examiner*—Kamal A. Saeed
*Assistant Examiner*—Michael Barker
(74) *Attorney, Agent, or Firm*—McDonnell Boehnen Hulbert & Berghoff LLP

(57) ABSTRACT

Disclosed are compounds of the Formula (I) and pharmaceutically acceptable salts and prodrugs thereof, wherein A, B, $R^1$, $R^2$, $R^3$, and $R^4$ are as defined in the specification. Such compounds are tyrosine phosphatase inhibitors and useful in the treatment or prevention of Type II Diabetes Mellitus. Also encompassed by the invention are formulations comprising the noted compounds, processes for preparing such compounds, a method for treating or preventing Type II Diabetes Mellitus

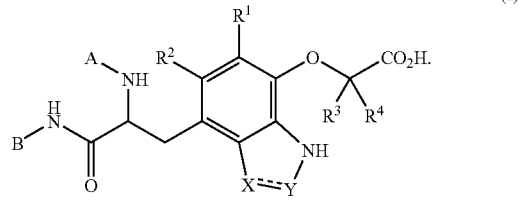

15 Claims, No Drawings

PREPARATION OF PHOSPHATASE INHIBITORS

BACKGROUND OF THE INVENTION

1. Field of the Invention

This invention relates to the preparation of phosphatase inhibitors that act as phosphotyrosine mimetics. The invention particularly relates to compounds designed to inhibit protein-tyrosine phosphatase 1B, and for the treatment of diabetes.

2. Summary of the Related Art

Protein tyrosine kinases (PTK) and protein tyrosine phosphatases (PTP) play an essential role in the regulation of various cellular functions including cell growth, proliferation, differentiation, metabolism and immune responses. They are therefore potentially important targets for therapeutic intervention in a number of diseases, including cancers and diabetes. PTKs generate phosphotyrosyl (pTyr) residues by mediating the phosphorylation of tyrosyl residues. PTPs, in turn, remove pTyr phophates and may play either positive or negative roles in cellular signal transduction.

At present, about 100 enzymes comprise the PTP family and each is either receptor-like or cytoplasmic. One such enzyme is PTP1B, a prototypic intracellular PTP that is expressed in many human tissues and is implicated as a negative regulator of insulin receptor signaling. Recent studies have shown that a correlation exists between levels of PTP1B and insulin resistance states, suggesting that PTP1B may play a role in the insulin resistance associated with diabetes and obesity. Apparently, PTP1B plays a vital role in the dephosphorylation of the insulin receptor. Further, a knockout study has revealed that mice lacking functional PTP1B exhibit increased sensitivity toward insulin and are resistant to obesity (Elchebly, M. et al., *Science* 1999, 283, 1544–1548). These studies suggest that PTP1B inhibitors would be useful in the treatment of insulin resistance and obesity. More importantly, such an inhibitor could function as an agent for the treatment of non-insulin dependent diabetes mellitus without inducing hypoglycemia.

To date, many of the previously reported PTP1B inhibitors have been peptide-based, containing negatively charged sulfate or phosphonic acid derivatives. Most of these compounds have been found to be inefficient in crossing cell membranes and are unstable in vivo. More recently, small organic molecules have been identified as potent and selective inhibitors of PTP1B (Larsen, S. et al. WO 00/53583; Larsen, S. et al., WO 99/11606; Sarmieto, M. et al., *J. Med. Chem.* 2000, 43, 146–155; Wrobel, J. et al., *J. Med. Chem.* 1999, 42, 3199–3202). Still desired is a PTP1B inhibitor that is even less peptidic in nature such that it increases solubility, absorption, cellular penetration and oral availability.

SUMMARY OF THE INVENTION

This invention provides certain tyrosine analogs of Formula I that are useful for treating Type II diabetes mellitus. Specifically, the present invention relates to compounds of Formula I that inhibit the protein tyrosine phosphatase 1B enzyme. Also provided are formulations containing compounds of Formula I and methods of using the compounds to treat a patient in need thereof. In addition, there are described processes for preparing the inhibitory compounds of Formula I.

The present invention relates to PTP1B inhibitors, pharmaceutically acceptable salts and prodrugs thereof useful in the therapeutic or prophylactic treatment of Type II diabetes mellitus. The invention also encompasses pharmaceutical compositions and methods for the treatment of Type II diabetes mellitus.

Accordingly, the compounds of the invention are members of the class of compounds of Formula I:

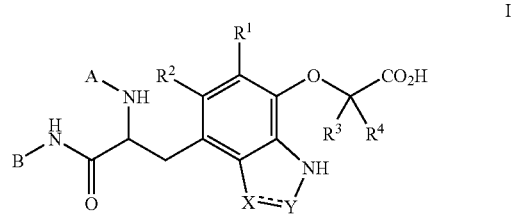

wherein

---- is an optional bond;

$R^1$ and $R^2$ are independently selected from hydrogen, hydroxy, halogen, lower alkyl, lower alkoxy, alkoxyalkyl, hydroxyalkyl, lower alkenyl, amino, mono- or dialkylamino, cyano, nitro, trifluromethyl, —CON($R^6$)$_2$ or —COO$R^6$;

$R^3$ and $R^4$ are independently selected from hydrogen, halogen, lower alkyl, lower alkenyl, cycloalkyl, cyano, —CON(R6)$_2$ or —COO$R^6$;

A is selected from lower alkyl, lower alkenyl, lower alkynyl, —C(O)$R^7$, —S(O)$_2R^7$, —C(O)NH$R^7$, —CO$_2R^7$, —(CH$_2$)$_n$S(O)$_qR^7$, —(CH$_2$)$_pC$(O)$R^7$, —(CH$_2$)$_pC$(O)NH$R^7$, —(CH$_2$)$_pCO_2R^7$, (CH$_2$)$_n$O$R^7$, or
 aryl, heteroaryl, arylalkyl or heteroarylalkyl, where the ring portion of each is optionally substituted with one, two or three groups independently selected from halogen, lower alkyl, hydroxy, amino, mono- or dialkylamino, trifluoromethyl, —C(O)$R^8$, —COO$R^8$, —C(O)NH$R^8$ or —O$R^8$;

B is selected from hydrogen, lower alkyl, lower alkenyl, lower alkynyl, —(CH$_2$)$_n$S(O)$_qR^7$, —(CH$_2$)$_pC$(O)$R^7$, —(CH$_2$)$_pC$(O)NH$R^7$, —(CH$_2$)$_pCO_2R^7$, (CH$_2$)$_n$O$R^7$, or
 aryl, heteroaryl, arylalkyl, arylalkenyl, arylalkynyl, heteroarylalkyl, heteroarylalkenyl or heteroarylalkynyl, where the ring portion of each is optionally substituted with one, two or three groups independently selected from halogen, lower alkyl, hydroxy, amino, mono- or dialkylamino, trifluoromethyl, —C(O)$R^8$, —COO$R^8$, —C(O)NH$R^8$ or —O$R^8$;

n is 2–4;

p is 1–2;

q is 0–2;

$R^6$ is selected from hydrogen, lower alkyl, or lower alkenyl;

$R^7$ is selected from aryl, heteroaryl, arylalkyl, or heteroarylalkyl, where the ring portion of each is optionally substituted with one, two or three groups independently selected from halogen, lower alkyl, hydroxy, amino, mono- or dialkylamino, trifluoromethyl, —C(O)$R^8$, —COO$R^8$, —C(O)NH$R^8$ or —O$R^8$;

$R^8$ is independently selected from hydrogen, or lower alkyl, aryl or heteroaryl optionally substituted with one, two or three groups
 independently selected from lower alkyl, halogen, lower alkoxy, hydroxy, amino, mono- or dialkylamino, or trifluoromethyl;

X and Y are nitrogen or CR$^{10}$; and $R^{10}$ is selected from hydrogen, hydroxy, halogen or amino.

DETAILED DESCRIPTION OF THE INVENTION

The novel compounds encompassed by the instant invention are those described by the general Formula I set forth above, and the pharmaceutically acceptable salts and prodrugs thereof.

Preferred compounds of Formula I are those in which the fused-ring system forms groups selected from indole, indazole, indoline, benzotriazole or benzoimidazole, each of which may be optionally substituted with one, two or three groups selected from —OH, halogen, amino, lower alkyl or oxo. More preferred groups are indole and indazole.

Accordingly, the invention also includes compounds of the Formula Ia:

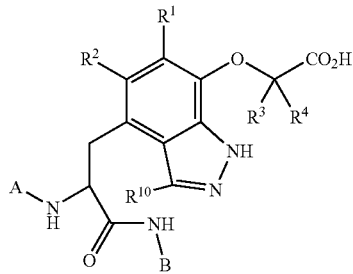

where $R^1$, $R^2$, $R^3$, $R^4$, $R^{10}$, A and B are as defined above for Formula I.

In a preferred embodiment of Formula Ia, $R^1$ is selected from hydrogen, halogen and methyl; $R^2$ is selected from hydrogen and halogen; $R^3$ is selected from hydrogen and fluorine; $R^4$ is hydrogen; A is —C(O)$R^7$ or —S(O)$_2R^7$; B is selected from lower alkyl, aryl-$C_{2-6}$-alkyl, 5–6-membered heteroaryl-$C_{2-6}$-alkyl, and $(CH_2)_nOR^7$; $R^7$ is aryl, 5–6 membered heteroaryl, aryl-$C_{1-3}$-alkyl, heteroaryl-$C_{1-3}$-alkyl; and n is 2–4.

The invention also includes compounds of the Formula Ib:

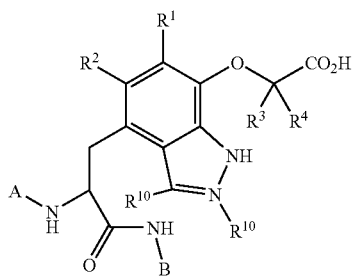

where $R^1$, $R^2$, $R^3$, $R^4$, each $R^{10}$ independently, A and B are as defined above for Formula I.

In a preferred embodiment of Formula Ib, $R^1$ is selected from hydrogen, halogen and methyl; $R^2$ is selected from hydrogen and halogen; $R^3$ is selected from hydrogen and fluorine; $R^4$ is hydrogen; A is —C(O)$R^7$ or —S(O)$_2R^7$; B is selected from lower alkyl, aryl-$C_{2-6}$-alkyl, 5–6-membered heteroaryl-$C_{2-6}$-alkyl, and $(CH_2)_nOR^7$; $R^7$ is aryl, 5–6 membered heteroaryl, aryl-$C_{1-3}$-alkyl, heteroaryl-$C_{1-3}$-alkyl; each $R^{10}$ is independently hydrogen or a halogen; and n is 2–4.

The invention further includes compounds of the Formula Ic:

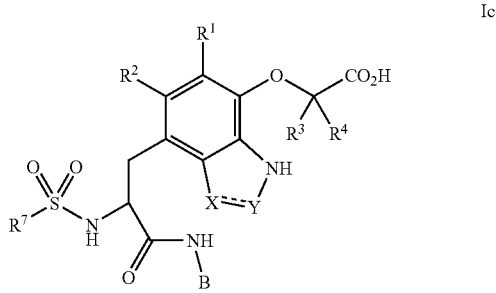

where $R^1$, $R^2$, $R^3$, $R^4$, $R^7$, X, Y and B are as defined above for Formula I.

In a preferred embodiment of Formula Ic, the optional bond ⁓ is present; $R^1$ is selected from hydrogen, halogen and methyl; $R^2$ is selected from hydrogen and halogen; $R^3$ is selected from hydrogen and fluorine; $R^4$ is hydrogen; B is selected from lower alkyl, aryl-$C_{2-6}$-alkyl, 5–6-membered heteroaryl-$C_{2-6}$-alkyl, and $(CH_2)_nOR^7$; $R^7$ is aryl, 5–6membered heteroaryl, aryl-$C_{1-3}$-alkyl, heteroaryl-$C_{1-3}$-alkyl; X is —$CR^{10}$, wherein $R^{10}$ is hydrogen or halogen; Y is nitrogen or —$CR^{10}$, wherein $R^{10}$ is hydrogen; and n is 2–4.

Except as expressly defined otherwise, the following definition of terms is employed throughout this specification.

By "alkyl" and "lower alkyl" in the present invention is meant straight or branched chain alkyl groups having 1–6 carbon atoms, such as, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. More preferred alkyl radicals are $C_{1-3}$alkyl.

By "alkoxy" and "lower alkoxy" in the present invention is meant straight or branched chain alkyl groups having 1–6 carbon atoms, attached through a divalent oxygen atom, such as, for example, methoxy, ethoxy, propoxy, isopropoxy, n-butoxy, sec-butoxy, tert-butoxy, pentoxy, isopentoxy, neopentoxy, hexoxy, and 3-methylpentoxy. More preferred are $C_{1-3}$alkoxy.

By "alkylthio" and "lower alkylthio" in the present invention is meant straight or branched chain alkyl groups having 1–6 carbon atoms, attached through a divalent sulfur atom, such as, for example, methylthio, ethylthio, propylthio, isopropylthio, n-butylthio, sec-butylthio, tert-butylthio, pentylthio, isopentylthio, neopentylthio, hexylthio, and 3-methylpentylthio. More preferred are $C_{1-3}$alkylthio.

"Alkenyl" means straight and branched hydrocarbon radicals having from 2–6 carbon atoms and at least one double bond and includes ethenyl, propenyl, 1-but-3-enyl, 1-pent-3-enyl, 1-hex-5-enyl and the like. More preferred are lower alkenyl having 3–5 carbon atoms.

"Alkynyl" means straight and branched hydrocarbon radicals having from 2–6 carbon atoms and one terminal triple bond and includes ethynyl, propynyl, butynyl, pent-2-ynyl and the like. More preferred are alkynyl having 3–5 carbon atoms.

By the term "halogen" in the present invention is meant fluorine, bromine, chlorine, and iodine.

By "heteroaryl" is meant one or more aromatic ring systems of 5-, 6-, or 7-membered rings which includes fused ring systems of 9–11 atoms containing at least one and up to four heteroatoms selected from nitrogen, oxygen, or sulfur. Such heteroaryl groups include, for example, thienyl, furanyl, thiazolyl, imidazolyl, (is)oxazolyl, pyridyl, pyrimidinyl, (iso)quinolinyl, napthyridinyl, benzimidazolyl, benzoxazolyl. More preferred heteroaryl groups are 5-, or 6 membered radicals. Heteroaryl groups are optionally mono-, di-, or trisubstituted with, e.g., halogen, lower alkyl, lower alkoxy, lower alkylthio, haloalkyl, aryl, heteroaryl, and hydroxy.

By "aryl" is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl), which is optionally mono-, di-, or trisubstituted with, e.g., halogen, lower alkyl, lower alkoxy, lower alkylthio, trifluoromethyl, aryl, heteroaryl, and hydroxy.

The terms "aralkyl" or "arylalkyl" means an alkyl moiety substituted with at least one aryl moiety. Preferred aralkyl radicals are aryl-$C_{1-3}$-alkyl. Examples include benzyl, phenylethyl, and the like.

The term "heteroarylalkyl" means an alkyl moiety substituted with at least one heteroaryl moiety. Preferred heteroarylalkyl radicals are 5- or 6-membered heteroaryl-$C_{1-3}$-alkyl. Examples include, oxazolemethyl, pyridylethyl and the like.

The term "alkylamino" means an amino moiety substituted with one or two alkyl moieties. Preferred alkylamino radicals are $C_{1-3}$-alkylamino. Examples include, methylamino, ethylamino, dimethylamino and the like.

The term "haloalkyl" means an alkyl moiety substituted with one or more halo moieties. Preferred haloalkyl radicals are halo-$C_{1-3}$-alkyl. Examples include chloromethyl, 1,1-difluoropropyl, and the like.

The term "arylalkenyl" means an alkenyl moiety substituted with at least one aryl moiety. Preferred arylalkenyl radicals are aryl-$C_{3-5}$-alkenyl. Examples include phenylethenyl, napthylethenyl, and the like.

The term "arylalkynyl" means an alkynyl moiety substituted with at least one aryl moiety. Preferred arylalkynyl radicals are aryl-$C_{3-5}$-alkynyl. Examples include phenylethynyl, napthylethynyl, and the like.

The term "heteroarylalkenyl" means an alkenyl moiety substituted with at least one heteroaryl moiety. Preferred heteroarylalkenyl radicals are 5- or 6-membered heteroaryl-$C_{3-5}$-alkenyl. Examples include, oxazolethenyl, pyridylethenyl and the like.

The term "heteroarylalkynyl" means an alkynyl moiety substituted with at least one heteroaryl moiety. Preferred heteroarylalkynyl radicals are 5- or 6-membered heteroaryl-$C_{3-5}$-alkynyl. Examples include, oxazolethynyl, pyridylethynyl and the like.

The term "cycloalkyl" means a carbocyclic group having a single ring (e.g., cyclohexane), multiple rings (e.g., dicyclohexyl), or multiple condensed rings in which none of the rings are aromatic, (e.g., adamantane), which is optionally mono-, di-, or trisubstituted with, e.g., halogen, lower alkyl, lower alkoxy, lower alkylthio, trifluoromethyl, aryl, heteroaryl, and hydroxy.

By "carbocycle" is meant a carbocyclic group having from 5–7 members (or as specifically defined) up to two of which members are optionally hetero atoms selected from oxygen, sulfur and nitrogen. In addition, the carbocyclic group may contain one or two double bonds. Thus, the carbocycle may or may not be aromatic, and if the carbocycle is fused to another ring, the carbocycle may or may not render the fused structure aromatic. Carbocycles are optionally mono-, di-, or trisubstituted with, e.g., halogen, lower alkyl, lower alkoxy, lower alkylthio, haloalkyl, aryl, heteroaryl, and hydroxy.

The following abbreviations, where appropriate, are defined below.

dec Decomposes
mp Melting point
RT Room temperature
THF Tetrahydrofuran
TLC Thin layer chromatography
HOAc Acetic acid
$CHCl_3$ Chloroform
$CH_2Cl_2$ Methylene chloride
CBz Carbobenzyloxy
DCM Dichloromethane
DIEA Diethylamine
DMF N,N'-Dimethylformamide
EDC 1-(3-Dimethylaminopropyl)-3-ethylcarbodiimide hydrochloride
EtOAc Ethyl acetate
EtOH Ethanol
$Et_2O$ Diethyl ether
HCl Hydrochloric acid
$H_2O_2$ Hydrogen peroxide
$H_2SO_4$ Sulfuric acid
KOH Potassium hydroxide
$CH_3CN$ Acetonitrile
MeOH Methanol
$K_2CO_3$ Potassium carbonate
NaCl Sodium chloride
NaOH Sodium hydroxide
$NaHCO_3$ Sodium carbonate
TFA Trifluoroacetic acid
Boc t-Butyloxycarbonyl "Pharmaceutically acceptable salt" as used herein refers to an organic or inorganic salt which is useful in the treatment of a warm-blooded animal. Such salts can be acid or basic addition salts, depending on the nature of the compound of Formula I. As used herein, "warm blooded animal" includes a mammal, including a member of the human, equine, porcine, bovine, murine, canine or feline species.

In the case of an acidic moiety in a compound of Formula I, a salt may be formed by treatment of a compound of Formula I with a basic compound, particularly an inorganic base. Preferred inorganic salts are those formed with alkali and alkaline earth metals such as lithium, sodium, potassium, barium and calcium. Preferred organic base salts include, for example, ammonium, dibenzylammonium, benzylammonium, 2-hydroxyethylammonium, bis(2-hydroxyethyl)ammonium, phenylethylbenzylamine, dibenzyl-ethylenediamine, and the like salts. Other salts of acidic moieties may include, for example, those salts formed with procaine, quinine and N-methylglusoamine, plus salts formed with basic amino acids such as glycine, ornithine, histidine, phenylglycine, lysine and arginine. An especially preferred salt is a sodium or potassium salt of a compound of Formula I.

With respect to basic moieties, a salt is formed by the treatment of a compound of Formula I with an acidic compound, particularly an inorganic acid. Preferred inorganic salts of this type may include, for example, the hydrochloric, hydrobromic, hydroiodic, sulfuric, phosphoric or the like salts. Preferred organic salts of this type, may include, for example, salts formed with formic, acetic, succinic, citric, lactic, maleic, fumaric, palmitic, cholic, pamoic, mucic, d-glutamic, d-camphoric, glutaric, glycolic, phthalic, tartaric, lauric, stearic, salicyclic, methanesulfonic, benzenesulfonic, paratoluenesulfonic, sorbic, puric, benzoic, cinnamic and the like organic acids. An especially preferred salt of this type is a hydrochloride or sulfate salt of a compound of Formula I.

Also encompassed in the scope of the present invention are pharmaceutically acceptable esters of a carboxylic acid or hydroxyl containing group, including a metabolically labile ester or a prodrug form of a compound of Formula I. A metabolically labile ester is one which may produce, for example, an increase in blood levels and prolong the efficacy of the corresponding non-esterified form of the compound. A prodrug form is one that is not in an active form of the molecule as administered but which becomes therapeutically active after some in vivo activity or biotransformation, such as metabolism, for example, enzymatic or hydrolytic cleavage. Esters of a compound of Formula I, may include, for example, the methyl, ethyl, propyl, and butyl esters, as well as other suitable esters formed between an acidic moiety and a hydroxyl containing moiety. Metabolically labile esters, may include, for example, methoxymethyl, ethoxymethyl, iso-propoxymethyl, α-methoxyethyl, groups such as α-((C1–C4)alkyloxy)ethyl; for example, methoxyethyl, ethoxyethyl, propoxyethyl, isopropoxyethyl, etc.; 2-oxo-1,3-dioxolen-4-ylmethyl groups, such as 5-methyl-2-oxo-1,3,dioxolen-4-ylmethyl, etc.; C1–C3 alkylthiomethyl groups, for example, methylthiomethyl, ethylthiomethyl, isopropylthiomethyl, etc.; acyloxymethyl groups, for example, pivaloyloxymethyl, α-acetoxymethyl, etc.; ethoxycarbonyl-1-methyl; or α-acyloxy-α-substituted methyl groups, for example α-acetoxyethyl.

Additionally, the compounds of the instant invention may have one or more asymmetrical carbon atoms and, therefore, may exist in stereoisomeric forms. AR stereoisomers are intended to be included within the scope of the present invention. As used, "stereoisomer" or "stereoisomeric" refers to a compound which has the same molecular weight, chemical composition, and constitution as another, but with the atoms grouped such that their orientation in three-dimensional space is different. Such stereoisomers may exist as enantiomeric mixtures, diastereomers or may be resolved into individual stereoisomeric components (e.g. specific enantiomers) by methods familiar to one skilled in the art.

Additionally the present invention includes all possible tautomers thereof.

Further, the compounds of the invention may exist as crystalline solids which can be crystallized from common solvents such as ethanol, N,N-dimethylformamide, water, or the like. Thus, crystalline forms of the compounds of the invention may exist as solvates and/or hydrates of the parent compounds or their pharmaceutically acceptable salts. All of such forms likewise are to be construed as falling within the scope of the invention.

In another aspect, the compounds of the invention are useful for the therapeutic or prophylactic treatment of Type II diabetes mellitus. The compounds of the invention may be also be used as PTP1B inhibitory agents in other diseases, such as, for example, different type of cancers, insulin resistance and obesity. The term "cancer" includes, but is not limited to, the following cancers: breast, ovary, cervix, prostate, testis, esophagus, glioblastoma, neuroblastoma, stomach, skin, keratoacanthoma, lung, epidermoid carcinoma, large cell carcinoma, adenocarcinoma, bone, colon, adenocarcinoma, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkins, hairy cells, buccal cavity and pharynx (oral), lip, tongue, mouth, pharynx, small intestine, colon-rectum, large intestine, rectum, brain and central nervous system; and leukemia.

While it may be possible to administer a compound of the invention alone, normally it will be present as an active ingredient in a pharmaceutical formulation. Thus, in one another embodiment of the invention, there is provided a formulation comprising a compound of Formula I in combination, admixture, or associated with a pharmaceutically acceptable carrier, diluent or excipient therefor.

The composition used in the noted therapeutic methods can be in a variety of forms. These include, for example, solid, semi-solid and liquid dosage forms, such as tablets, pills, powders, liquid solutions or suspensions, liposomes, injectable and infusible solutions. The preferred form depends on the intended mode of administration and therapeutic application. Considerations for preparing appropriate formulations will be familiar to one skilled in the art and are described, for example, in Goodman and Gilmans: "The Pharmacological Basis of Therapeutics", 8th Ed., Pergamon Press, Gilman et al. eds. (1990); and "Remington's Pharmaceutical Sciences", 18th Ed., Mack Publishing Co., A. Gennaro, ed. (1990). Methods for administration are discussed therein, eq. for oral, topical, intravenous, intraperitoneal, or intramuscular administration. Pharmaceutically acceptable carriers, diluents, and excipients, likewise, are discussed therein. Typical carriers, diluents, and excipients may include water (for example, water for injection), buffers, lactose, starch, sucrose, and the like.

As noted, a compound of the invention can be administered orally, topically or parenterally (e.g. intravenously, intraperitoneally, intramuscularly, subcutaneously, etc.), or inhaled as a dry powder, aerosol, or mist, for pulmonary delivery. Such forms of the compounds of the invention may be adminstered by conventional means for creating aerosols or administering dry powder medications using devices such as for example, metered dose inhalers, nasal sprayers, dry powder inhaler, jet nebulizers, or ultrasonic nebulizers. Such devices optionally may be include a mouthpiece fitted around an orifice. In certain circumstances, it may be desirable to administer the desired compound of the invention by continuous infusion, such as through a continuous infusion pump, or using a transdermal delivery device, such as a patch.

In a further embodiment of the invention, there is provided a pharmaceutical preparation for topical application comprising a compound of the invention, typically in concentrations in the range of from about 0.001% to about 10%, in combination with a pharmaceutically acceptable carrier, excipient, or diluent therefor. Such topical preparations can be prepared by combining the compound of the invention with conventional pharmaceutical diluents and carriers commonly used in topical dry, liquid, cream and aerosol formulations. Ointment and creams may be formulated, for example, with an aqueous or oily base with the addition of suitable thickening and/or gelling agents. Such bases may include water and/or an oil such as a liquid paraffin or a vegetable oil such as peanut oil or castor oil. Thickening agents which may be used according to the characteristics of the base may include, for example, soft paraffin, aluminum stearate, cetostearyl alcohol, propylene glycol, polyethylene glycols, woolfat, hydrogenated lanolin, beeswax, and the like.

Lotions may be formulated with an aqueous or oily base and will include also, in general, one or more of the following: stabilizing agents emulsifying agents, dispersing agents, suspending agents, thickening agents, coloring agents, perfumes, and the like. Powders may be formed with the aid of any suitable powder bases, for example, talc, lactose, starch and the like. Drops may be formulated with an aqueous base or non-aqueous base also comprising one or more dispersing agents, suspending agents solubilizing agents, and the like.

Any of the formulations of the invention may also include one or more preservatives or bacteriostatic agents, for example, methyl hydroxybenzoate, ethyl hydroxybenzoate, propyl hydroxybenzoate, chlorocresol, benzalkonium chlorides, and the like. Additionally, the formulations may contain other active ingredients such as antimicrobial agents, particularly antibiotics, anesthetics, analgesics and antipruritic agents.

The pharmaceutical formulations of the invention may be administered by parenteral or oral administration for prophylactic and/or therapeutic treatment. The pharmaceutical compositions can be administered in a variety of unit dosage forms depending on the method of administration. For example, unit dosage forms suitable for oral administration may include, powders, tablets, pills, capsules and dragées.

The pharmaceutical formulations can be administered intravenously. Therefore, the invention further provides formulations for intravenous administration which comprise a compound of the invention dissolved or suspended in a pharmaceutically acceptable carrier or diluent therefor. A variety of aqueous carriers can be used, for example, water, buffered water or other buffer solutions, saline, and the like. The resulting aqueous solutions can be packaged for use as is, or lyophilized, the lyophilized preparation being combined with a sterile aqueous solution prior to administration. The sterile aqueous solution for the lyophilized product can be packaged as a kit for use with the lyophilized formulation. The compositions can contain pharmaceutically acceptable substances to aid in administration and more closely mimic physiological conditions. Such substances, can include, for example, pH adjusting substances such as acids, bases or buffering agents, tonicity adjusting agents, wetting agents and the like. Such substances may include but are not limited to, for example, sodium hydroxide, hydrochloric acid, sulfuric acid, sodium acetate, sodium lactate, sodium chloride, potassium chloride, calcium chloride, sorbitan monolaurate, triethanolamine oleate, and the like or any other means familiar to one skilled in the art for maintaining pH at a desired level.

For solid formulations, carriers, diluents, and excipients known to one skilled in the art may be used. Such carriers, diluents and excipients may include, for example, mannitol, lactose, starch magnesium stearate, sodium saccharin, talcum, cellulose, glucose, sucrose, or other solid polyol sugar, magnesium carbonate, and the like. For oral administration, a pharmaceutically acceptable formulation is prepared by admixing any of the usual carrier, diluents, and excipients, such as those noted, with from about 0.1 to about 95% of a compound of the invention.

The term "prodrug" refers to compounds that are rapidly transformed in vivo to yield the parent compound of the above formulae, for example, by hydrolysis in blood. A thorough discussion is provided in T. Higuchi and V Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference.

An illustration of the preparation of the compounds of the present invention is shown in Schemes 1–3. $R^1$, $R^2$, A and B are as defined above for Formula I, X is a suitable leaving group, including but not limited to a halide, a mesylate or a tosylate, and "Prot" is a suitable protecting group readily introduced on to and removed from the atom to which it is attached (suitable protecting groups to those skilled in the art are found in "Protective Groups in Organic Synthesis", 3rd Ed., Greene, T. W, et al). The c ring can be synthesized, as exemplified in Scheme 1 for indazoles, or starting material can be purchased with the c ring in place.

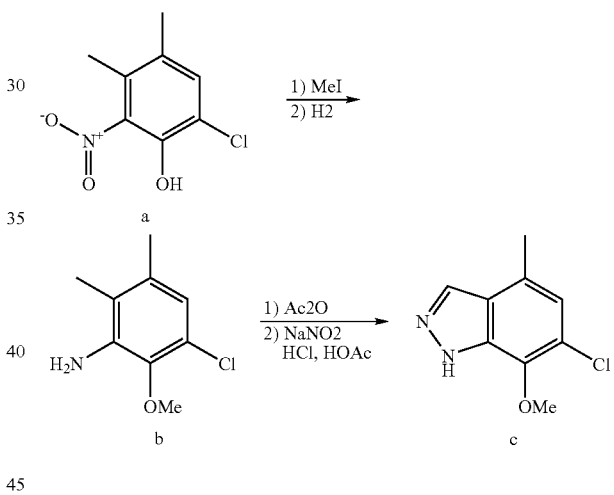

Introduction of the A and B substituents can be achieved, for example, by displacing a leaving group on the benzylic carbon of the desired fused bicycle d with a benzhydrylideneamino acetamide. Subsequent hydrolysis of the Schiff base e allows for introduction of many A groups, as, for example, the sulfonamide f produced in Scheme 2.

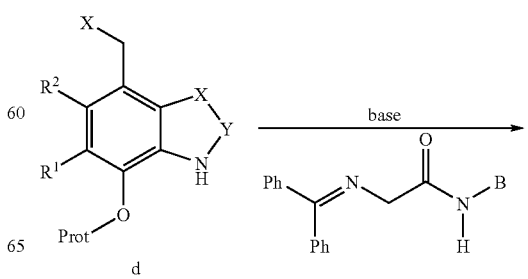

-continued

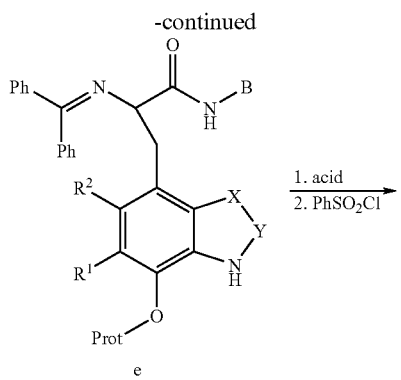

e

X = leaving group
Prot = Protecting group

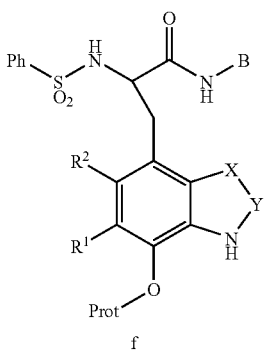

f

In Scheme 3, the acetate is then produced by alkylating the phenol h with a reagent such as, for example, bromomethyl acetate. A protected phenol g may first be deprotected if necessary. The ester can then be saponified to the acid j.

Scheme 3

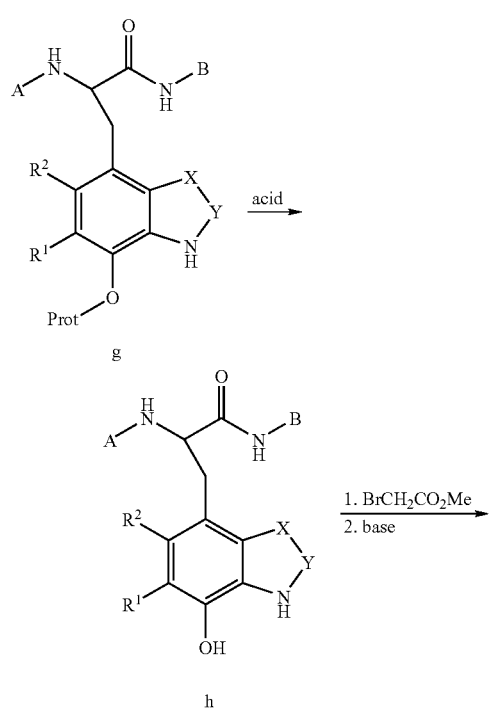

-continued

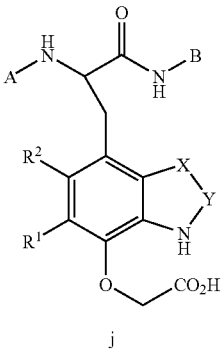

j

The disclosures in this application of all articles and references, including patents, are incorporated herein by reference.

The invention is illustrated further by the following examples which are not to be construed as limiting the invention in scope or spirit to the specific procedures described in them.

The starting materials and various intermediates may be obtained from commercial sources, prepared from commercially available organic compounds, or prepared using well known synthetic methods.

Representative examples of methods for preparing intermediates of the invention are set forth below.

EXAMPLES

Example 1

{4-[2-Benzenesulfonylamino-2-(4-phenyl-butylcarbamoyl)-ethyl]-1H-indazol-7-yloxy}-acetic acid (1)

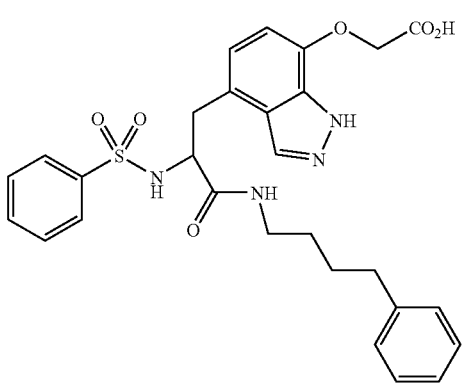

Step A:
3-Chloro-2-methoxy-5,6-dimethyl-phenylamine

1-Chloro-2-methoxy-4,5-dimethyl-3-nitro-benzene (10.0 g, 46.4 mmol; Stachel et. al., *J. Org. Chem.* 1997, 46, 4756) is dissolved in MeOH (200 mL) in a 500 mL round bottom flask. The flask is purged with $N_2$ and 10% Pd on Carbon (0.7 g) is added and the reaction is again purged with $N_2$. The reaction is purged with $H_2$ and rapidly stirred for 15 h. The major product is the desired product from partial reduction. The reaction is filtered on celite and washed with MeOH and concentrated. Overreduction (des-chloro) product is filtered off as a solid from partially dissolving the crude reaction mixture in EtOH and MeOH to provide 3-chloro-2-methoxy-5,6-dimethyl-phenylamine which is used without further purification.

Step B: N-(3-Chloro-2-methoxy-5,6-dimethyl-phenyl)-acetamide

3-Chloro-2-methoxy-5,6-dimethyl-phenylamine (4.9 g, 26 mmol) is dissolved in dichloromethane (20 mL) and pyridine (8 mL) and cooled to 0° C. Acetic anhydride (3.7 mL, 39 mmol) and DMAP (85 mg, 0.7 mmol) are added and the reaction is allowed to warm to room temperature. After stirring 2 h, the reaction is diluted with EtOAc (500 mL) and washed with water, 2N HCl (2×50 mL), water, brine and dried over $MgSO_4$ and concentrated. The crude reaction mixture is dissolved in dichloromethane and a minimal amount of MeOH and then added to a dry pad of silica gel. The product is eluted with 50 to 80% EtOAc/hexanes to provide N-(3-chloro-2-methoxy-5,6-dimethyl-phenyl)-acetamide.

Step C: 6-Chloro-7-methoxy-4-methyl-1H-indazole

N-(3-Chloro-2-methoxy-5,6-dimethyl-phenyl)-acetamide (3.36 g, 17.4 mmol) is dissolved in HOAc (75 mL) and conc. HCl (30 mL) in a 1 L round bottom flask. The reaction is cooled to 0° C. with an ice/salt bath. Although some starting material crystallizes, a solution of $NaNO_2$ (5.9 g, 86 mmol) in water (25 mL) is added portion-wise over 5 min. All material goes into solution and the reacion is stoppered and stirred 45 min. HPLC shows very little sm. Ice cold water (800 mL) is was added slowly and the reaction was stirred 1 h. A precipitate forms. The solid is filtered and washed with ice cold water (500 mL). The material is dried with suction and then pumped to a constant weight 3.3 g. The solid is partially dissolved in toluene (35 mL) and stirred under $N_2$. After stirring 18 h, the reaction is heated for 4 hours and cooled. The reaction is diluted with EtOAc and washed with $NaHCO_3$, brine, dried ($MgSO_4$) and concentrated. The crude product is purified by column chromatography (silica, 30% EtOAc/hexanes) to provide the desired product, 6-chloro-7-methoxy-4-methyl-1H-indazole.

Step D: 1-Benzenesulfonyl-6-chloro-7-methoxymethyl-1H-indazole

6-Chloro-7-methoxy-4-methyl-1H-indazole (1.55 g, 9.2 mmol) is dissolved in THF (50 mL) and cooled to 0° C. Sodium hydride (60% in mineral oil, 0.40 g, 10 mmol) is added and the reaction is stirred 10 min. Benzenesulfonyl chloride (1.2 mL, 9.7 mmol) is added and the reaction is stirred 20 min. The reaction is diluted with EtOAc, washed with a solution of $NH_4Cl$, water, brine and dried with $MgSO_4$. The solution is concentrated and triturated with hexane to provide 1-benzenesulfonyl-6-chloro-7-methoxy-4-methyl-1H-indazole which is used without further purification.

Step E: 1-Benzenesulfonyl-4-bromomethyl-6-chloro-7-methoxy-1H-indazole

1-Benzenesulfonyl-6-chloro-7-methoxy-4-methyl-1H-indazole (2.45 g, 7.3 mmol), recrystallized N-bromosuccinimide (1.36 g, 7.6 mmol) and benzoyl peroxide (90 mg, 0.37 mmol) are dissolved in carbon tetrachloride (25 mL). The reaction is degassed and then placed in a 80° C. bath. The reaction is heated (about 2 h) until no starting material remains by TLC analysis (PhMe). The reaction is cooled, diluted with EtOAc, and washed with water. The solution is dried with $MgSO_4$, concentrated and purified by column chromatography (silica, PhMe) to provide 1-benzenesulfonyl-4-bromomethyl-6-chloro-7-methoxy-1H-indazole.

Step F: 3-(1-Benzenesulfonyl-6-chloro-7-methoxy-1H-indazol-4-yl)-2-(diphenylmethylenamino)-N-(4-phenyl-butyl)-propionamide 2-(Diphenylmethylenamino)-N-(4-phenyl-butyl)-acetamide (7) (0.57 g, 1.5 mmol) is dissolved in dry THF (5 mL) and cooled to −78° C. A solution of KHMDS (0.5 M in PhMe, 3.0 mL, 1.5 mmol) is added slowly to the imide. The solution is warmed to 0° C. and then cooled to −78° C. A solution of 1-benzenesulfonyl-4-bromomethyl-6-chloro-7-methoxy-1H-indazole (0.57 g, 1.4 mmol) in dry THF (4 mL) is added slowly at −78° C. and the solution is allowed to stir 15 min. The reactio is then poured into a solution of aqueous $NH_4Cl$ and extracted with EtOAc. The organic phase is washed with water, brine, dried over MgSO4 and concentrated. The crude reaction is purified by column chromatography (silica, 10–20% EtOAc/PhMe) to provide 3-(1-benzenesulfonyl-6-chloro-7-methoxy-1H-indazol-4-yl)-2-(diphenylmethylenamino)-N-(4-phenyl-butyl)-propionamide.

Step G: 2-Amino-3-(1-benzenesulfonyl-6-chloro-7-methoxy-1H-indazol-4-yl)-N-(4-phenyl-butyl)-propionamide hydrochloride 3-(1-Benzenesulfonyl-6-chloro-7-methoxy-1H-indazol-4-yl)-2-(diphenylmethylenamino)-N-(4-phenyl-butyl)-propionamide (0.46 g, 0.65 mmol) is dissolved in $Et_2O$ (15 mL) and rapidly stirred with 2N HCl for 14 hours. The ether layer was decanted and the remaining aqueous layer was washed with $Et_2O$. The aqueous layer was then concentrated and azeotroped to dryness with PhMe to provide 2-amino-3-(1-benzenesulfonyl-6-chloro-7-methoxy-1H-indazol-4-yl)-N-(4-phenyl-butyl)-propionamide hydrochloride which was used in the next step without further purification.

Step H: 2-Benzenesulfonylamino-3-(1-benzenesulfonyl-6-chloro-7-methoxy-1H-indazol-4-yl)-N-(4-phenyl-butyl)-propionamide 2-Amino-3-(1-benzenesulfonyl-6-chloro-7-methoxy-1H-indazol-4-yl)-N-(4-phenyl-butyl)-propionamide hydrochloride (0.31 g, 0.54 mmol) is dissolved in a mixture of dichloromethane (4 mL) and pyridine (1.5 mL). Benzenesulfonyl chloride (0.12 mL, 0.9 mmol) is added portionwise and the reaction is allowed to stir for a total of 18 h. The reaction is diluted with EtOAc and washed with water, 1N HCl three times, water, brine and dried over $MgSO_4$. The solution is concentrated and purified by column chromatography (silica, 5% EtOAc/$CH_2Cl_2$ to provide 2-benzenesulfonylamino-3-(1-benzenesulfonyl-6-chloro-7-methoxy-1H-indazolyl)-N-(4-phenyl-butyl)-propionamide.

Step I: 2-Benzenesulfonylamino-3-(6-chloro-7-methoxy-1H-indazol-4-yl)-N-(4-phenyl-butyl)-propionamide 2-Benzenesulfonylamino-3-(1-benzenesulfonyl-6-chloro-7-methoxy-1H-indazol-4-yl)-N-(4-phenyl-butyl)-propionamide (0.17 g, 0.25 mmol) is dissolved in MeOH (2 mL) and K₂CO₃ is added and the reaction is stirred for 1 h. The reaction is quenched by the addition of 2 N HCl (0.1 mL) and then concentrated. The residue is dissolved in EtOAc and washed with water, brine and dried over MgSO₄. The solution is concentrated and purified by column chromatography (silica, 60% EtOAc/hexanes) to provide 2-benzenesulfonylamino-3-(6-chloro-7-methoxy-1H-indazol-4-yl)-N-(4-phenyl-butyl)-propionamide.

Step J: 2-Benzenesulfonylamino-3-(6-chloro-7-hydroxy-1H-indazol-4-yl)-N-(4-phenyl-butyl)-propionamide 2-Benzenesulfonylamino-3-(6-chloro-7-methoxy-1H-indazol-4-yl)-N-(4-phenyl-butyl)-propionamide (0.10 g, 0.19 mmol) and pyridinium hydrochloride (ca. 0.7 g) are combined in a 2 mL pressure vial. The reaction is heated to obtain a melt (ca. 170° C. bath). After 50 min. the reaction is cooled and partitioned between EtOAc and NH₄Cl. The organic layer is washed with water, brine and dried over MgSO₄. The solution is concentrated and purified by column chromatography (silica, 4% MeOH/CH₂Cl₂) to provide 2-benzenesulfonylamino-3-(6-chloro-7-hydroxy-1H-indazol-4-yl)-N-(4-phenyl-butyl)-propionamide.

Step K: {4-[2-Benzenesulfonylamino-2-(4-phenyl-butylcarbamoyl)-ethyl]-6-chloro-1H-indazol-7-yloxy}-acetic acid 2-Benzenesulfonylamino-3-(6-chloro-7-hydroxy-1H-indazol-4-yl)-N-(4-phenyl-butyl)-propionamide (30 mg, 0.057 mmol) is dissolved in DMF (1 mL) and K₂CO₃ is added followed by a slight excess of methyl bromoacetate (11 mg, 0.072 mmol). The reaction is allowed to stir for 36 h. The reaction is worked-up by diluting with EtOAc and washing with NH4Cl, 0.5 N HCl, water and brine. The solution is dried with MgSO4 and concentrated to provide a mixture of the intermediate ester and desired acid product as observed by LC/MS. The acid is purified by chromatography using a 10 g C18 sep-pak column (CH₃CN/H₂O) to provide {4-[2-benzenesulfonylamino-2-(4-phenyl-butylcarbamoyl)-ethyl]-6-chloro-1H-indazol-7-yloxy}-acetic acid. ¹H NMR (500 MHz, DMSO-d₆) δ 8.17 (d, 1H), 8.29 (bs, 1H), 7.94 (dd, 1H), 7.46 (d, 2H), 7.42 (dd, 1H), 7.28–7.24 (m, 4H), 7.16–7.14 (m, 3H), 6.84 (s, 1H), 4.59 (bs, 2H), 4.19–4.15 (m, 1H), 4.01–3.95 (m, 1H), 3.03–2.97 (m, 1H), 2.90–2.79 (m, 3H), 2.50 (obs, 2H), 1.43–1.38 (m, 2H), 1.22–1.17 (m, 2H); MS (ESI+) m/z 585 (M+H).

The following compound can be prepared using similar chemistry to that which is described above in Example 1:

{4-[2-Benzenesulfonylamino-2-(4-phenyl-butylcarbamoyl)-ethyl]-6-chloro-1H-indazol-7-yloxy}-fluoro-acetic acid (2)

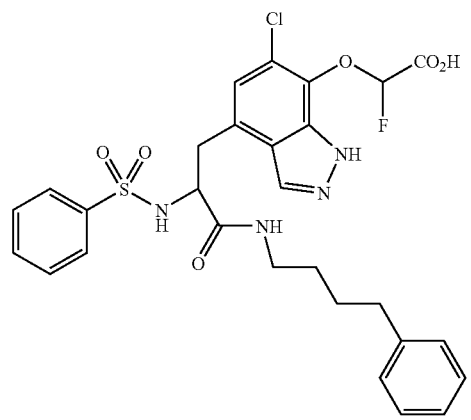

¹H NMR (400 MHz, MeOH-d₄) δ 8.00 (s, 1H), 7.53–7.45 (d, 2H), 7.40 (m, 1H), 7.27–7.21 (m, 4H), 7.1–7.13 (m, 3M, 6.88 (s, 1H), 5.83 and 5.70 (fluorine splitting, d, 1H), 4.00 (t, 1H), 3.30–3.22 (m, 1H), 3.15–2.90 (m, 3H), 2.59–2.52 (m, 2H), 1.52–1.45 (m, 2H), 1.28–1.24 (m, 2H); MS (ESI+) m/z 603 (M+H).

Example 2

{4-[2-Benzenesulfonylamino-2-(4-phenyl-butylcarbamoyl)-ethyl]-1H-indazol-7-yloxy}-acetic acid (1)

{4-[2-Benzenesulfonylamino-2-(4-phenyl-butylcarbamoyl)-ethyl]-6-chloro-1H-indazol-7-yloxy}-acetic acid (8.0 mg, 0.014 mmol) is dissolved in MeOH (1.5 mL) and 10% Pd/C (5 mg) is added. The reaction is purged with N₂ and then with H₂. The reaction is rapidly stirred and monitored by HPLC until complete (approximately 30 h). The reaction is filtered through celite and washed with MeOH to provide {4-[2-benzenesulfonylamino-2-(4-phenyl-butylcarbamoyl)-ethyl]-1H-indazol-7-yloxy}-acetic acid. ¹H NMR (500 MHz, MeOH-d₄) δ 7.88 (s, 1H), 7.49–7.47 (d, 2H), 7.40 (dd, 1H), 7.25–7.21 (m, 4H), 7.15–7.13 (m, 3H), 6.70 (d, 1H), 6.49 (d, 1H), 5.37 (m, 1H), 4.45 (s, 2H), 3.97 (t, 1H), 3.6 (obs, 1H), 3.14 (dd, 1H), 3.07–3.02 (m, 2H), 2.94–2.89 (m, 2H), 2.53 (t, 2H), 1.45–1.39 (m, 2H), 1.28–1.22 (m, 2H); MS (ESI+) m/z 551 (M+H).

The following compound can be prepared using similar chemistry to that which is described above:

{4-[2-Benzenesulfonylamino-2-(4-phenyl-butylcarbamoyl)-ethyl]-1H-indazol-7-yloxy}-fluoro-acetic acid (3)

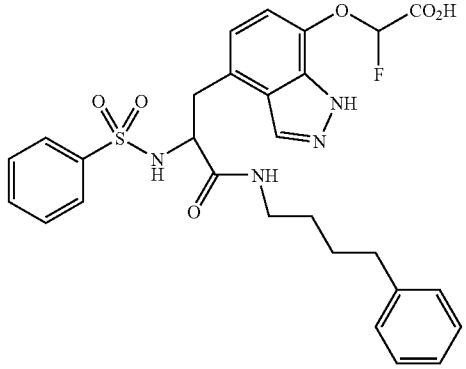

MS (ESI+) m/z 569 (M+H).

Example 3

{4-[2-Benzenesulfonylamino-2-(4-phenyl-butylcarbamoyl)-ethyl]-1H-indol-7-yloxy}-fluoro-acetic acid, sodium salt (4)

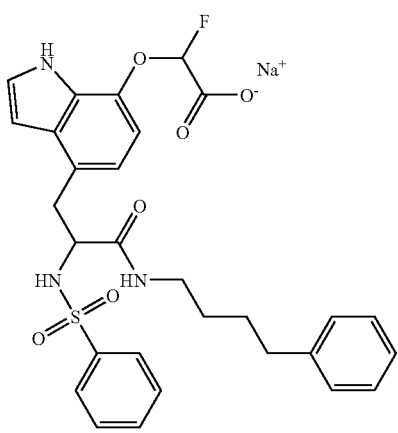

Step A: (1-Benzenesulfonyl-7-methoxy-1H-indol-1-yl)-methanol

Diisobutylaluminum hydride (1.5 M toluene, 1.4 mL, 2.1 mmol) is added dropwise to a −78° C. solution of 1-benzenesulfonyl-7-methoxy-1H-indole-4-carboxylic acid methyl ester (0.34 g, 0.98 mmol, Santangelo, et. al., Synth. Commun. 1993, 23, 2717–2725) in $CH_2Cl_2$ (7 mL). After stirring for 1 h, the solution is diluted with 10% aq. Rochelle's salt (100 mL) and extracted twice with EtOAc (100 mL). The organics are washed with aq. Rochelle's salt and brine. The organics are dried ($MgSO_4$) and concentrated under reduced pressure to provide (1-benzenesulfonyl-7-methoxy-1H-indol-4-yl)-methanol as a crispy foam which is used as is without further purification.

Step B: 2-Amino-3-(1-benzenesulfonyl-7-methoxy-1H-indol-1-yl)-N-(4-phenyl-butyl)-acetamide, hydrogen chloride salt Potassium bis(trimethyl)silylamide (0.5 M toluene, 30 mL, 15 mmol) is added dropwise to a −78° C. solution of 2-(diphenylmethylenamino)-N-(4-phenyl-butyl)-acetamide (7) (5.6 g, 15 mmol, example 4) in THF (30 mL). The solution is stirred 45 min.

Methanesulfonyl chloride (0.82 g, 7.2 mmol) is added dropwise to a 0° C. solution of (1-benzenesulfonyl-7-methoxy-1H-indol-4-yl)-methanol (1.9 g, 6.0 mmol) and Hunig's base (1.2 g, 9.0 mmol) in THF (20 mL). After stirring for 2 h, the mixture is added to the enolate solution described above. The resulting mixture is stirred 30 min at −78° C., then warmed to −30° C. over 1.5 h. The mixture is then diluted with diethyl ether and washed with a saturated $NaHCO_3$ solution. The aqueous phase is extracted once with diethyl ether. The organics are dried ($MgSO_4$) and concentrated. The residue is used as is without further purification.

The residue is dissolved in $Et_2O$ (40 mL) and stirred with 1 M HCl (40 mL) for 1 h. The resulting precipitate is collected by filtration, washed with diethyl ether, then azeotroped sequentially with MeOH, dioxane, toluene, and EtOAc to provide 2-amino-3-(1-benzenesulfonyl-7-methoxy-1H-indol-4-yl)-N-(4-phenyl-butyl)-propionamide, hydrogen chloride salt as a crispy foam which is used as is without further purification.

Step C: 2-Benzenesulfonylamino-3-(1-benzenesulfonyl-7-methoxy-1H-indol-4-yl)-N-(4-phenyl-butyl)-acetamide Hunig's base (2.1 g, 16 mmol) is added to a suspension of 2-amino-3-(1-benzenesulfonyl-7-methoxy-1H-indol-4-yl)-N-(4-phenyl-butyl)-propionamide, hydrogen chloride salt (3.0 g, 5.6 mmol) in $CH_2Cl_2$. The resulting solution is cooled to 0° C. and benzenesulfonyl chloride (1.2 g, 6.9 mmol) is added. After being warmed to rt and stirred 2 h, the reaction mixture is diluted with $Et_2O$ and washed sequentially with 0.5 M HCl and saturated $NaHCO_3$ solutions. The aqueous phases are extracted once with $Et_2O$. The desired compound crystallizes at this point. The volatiles are removed in vacuo and the remaining residue is azeotroped sequentially with dioxane and toluene to provide 2-benzenesulfonylamino-3-(1-benzenesulfonyl-7-methoxy-1H-indol-4-yl)-N-(4-phenyl-butyl)-propionamide as a solid which is used as is without further purification.

Step D: 2-Benzenesulfonylamino-3-(7-methoxy-1H-indol-4-yl)-N-(4-phenyl-butyl)-acetamide A mixture of 2-benzenesulfonylamino-3-(1-benzenesulfonyl-7-methoxy-1H-indol-4-yl)-N-(4-phenyl-butyl)-propionamide (1.0 g, 1.6 mmol) and 2.5 M KOH (2.0 mL, 5.0 mmol) is refluxed in MeOH (9 mL) for 22 h. The resulting solution is poured into a saturated $NH_4Cl$ solution and extracted twice with EtOAc. The organics are dried ($MgSO_4$) and concentrated to provide 2-benzenesulfonylamino-3-(7-methoxy-1H-indol-4-yl)-N-(4-phenyl-butyl)-propionamide as an oil which is used as is without further purification.

Step E: 2-Benzenesulfonylamino-3-(7-hydroxy-1H-indol-4-yl)-N-(4-phenyl-butyl)-acetamide Aluminum chloride (0.13 g, 0.99 mmol) is added to a 0° C. solution of 2-benzenesulfonylamino-3-(7-methoxy-1H-indol-4-yl)-N-(4-phenyl-butyl)-propionamide (0.12 g, 0.25 mmol) and EtSH (0.061 g, 0.99 mmol). The mixture is stirred 3.5 h while being allowed to warm to rt. Additional AlCl₃ (0.13 g, 0.99 mmol) and EtSH (0.061 g, 0.99 mmol) are added and the mixture is stirred 1 h more. The mixture is then poured into a saturated NH₄Cl solution and extracted twice with EtOAc. The organics are dried (MgSO₄) and concentrated. The crude residue is purified by column chromatography (silica, 1:3 EtOAc/CH₂Cl₂) to provide the title compound 2-benzenesulfonylamino-3-(7-hydroxy-1H-indol-4-yl)-N-(4-phenyl-butyl)-propionamide as an oil.

Step F: {4-[2-Benzenesulfonylamino-2-(4-phenyl-butylcarbamoyl)ethyl]-1H-indol-7-yloxy}-fluoro-acetic acid ethyl ester Sodium hydride (60% in oil, 2.8 mg, 0.069 mmol) is added to a solution of 2-benzenesulfonylamino-3-(7-hydroxy-1H-indol-4-yl)-N-(4-phenyl-butyl)-propionamide in 0.7 mL DMF. A solution of bromofluoro ethyl acetate (13 mg, 0.069 mmol) in DMF (0.2 mL) is added and the reaction is stirred 21 h at rt. Additional NaH (1.4 mg, 0.035 mmol) and bromofluoro ethyl acetate (6.5 mg 0.035 mmol) are added and the mixture is stirred 7 h more. The reaction is poured into 1 M HCl and extracted four times with EtOAc. The organics are dried (Na₂SO₄) and concentrated. The crude residue is purified by column chromatography (silica, 1:8 EtOAc/CH₂Cl₂) to provide {4-[2-benzenesulfonylamino-2-(4-phenyl-butylcarbamoyl)-ethyl]-1H-indol-7-yloxy}-fluoro-acetic acid ethyl ester as an oil.

Step G: {4-[2-Benzenesulfonylamino-2-(4-phenyl-butylcarbamoyl)-ethyl]-1H-indol-7-yloxy}-fluoro-acetic acid, sodium salt Sodium hydroxide (2.0 M, 1.0 mL, 2.0 mmol) is added to a solution of {4-[2-benzenesulfonylamino-2-(4-phenyl-butylcarbamoyl)-ethyl]-1H-indol-7-yloxy}-fluoro-acetic acid ethyl ester (16 mg, 0.027 mmol) in MeOH (1 mL). The solution is stirred at rt for 15 min, then concentrated in vacuo. The crude residue is purified by chromatography using a 10 g C18 sep-pak column (CH₃CN/H₂O) to provide the title compound {4-[2-benzenesulfonylamino-2-(4-phenyl-butylcarbamoyl)-ethyl]-1H-indol-7-yloxy}-fluoro-acetic acid, sodium salt. ¹H NM (400 MHz, MeOH-d₄) δ 7.43 (m, 3H), 7.15 (m, 8H), 6.62 (m, 2H), 6.35 (m, 1H), 5.96 and 5.80 (d, 1H), 4.00 (m, 1H), 3.23 (m, 1H), 3.03 (m, 1H), 2.90 (m, 2H), 2.54 (m, 2H), 1.45 (m, 2H), 1.30 (m, 2H); MS (ES+) m/z 568 (M—Na+2).

The following compounds can be prepared using similar chemistry to that which is described above:

{4-[2-Benzenesulfonylamino-2-(4-phenyl-butylcarbamoyl)-ethyl]-1H-indol-7-yloxy}-acetic acid (5)

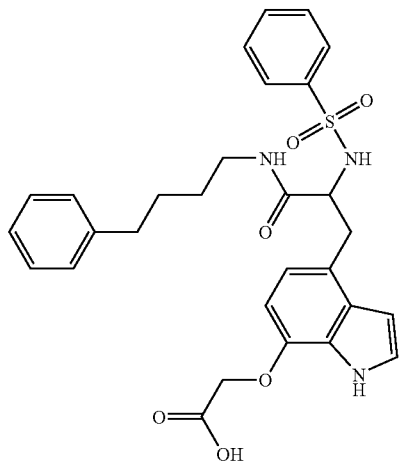

5

¹H NMR (400 MHz, MeOH-d₄) δ 7.70 (m, 1H), 7.47 (m, 2H), 7.39 (m, 2H), 7.24 (m, 4H), 7.14 (m, 4H), 6.60 (d, 1H), 6.32 (m, 2H), 4.68 (d, 2H), 3.96 (dd, 1H), 3.21 (dd, 1H), 3.05 (m, 1H), 2.86 (m, 2H, 2.51 (m, 2H) 1.41 (m, 2H), 1.28 (m, 2H); MS (ES+) m/z 550 (M+1).

{4-[2-Benzenesulfonylamino-2-(4-phenyl-butylcarbamoyl)-ethyl]-3-bromo-1H-indol-7-yloxy}-acetic acid (6)

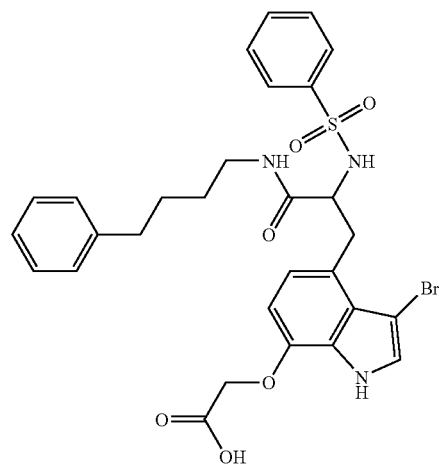

6

¹H NMR (400 MHz, MeOH-d₄) δ 7.45 (m, 2H), 7.38 (m, 1H), 7.20 (m, 8H), 6.58 (d, 1H), 6.33 (d, 1H), 4.40 (m, 2H), 4.10 (m, 1H), 4.68 (d, 2H), 3.43 (dd, 1H), 3.13 (m, 2H), 2.90 (m, 2H), 2.55 (m, 2H) 1.45 (m, 2H), 1.35 (m, 2H); MS (APCI+) m/z 629 (M+1).

Example 4

2-(Diphenylmethylenamino)-N-(4-phenyl-butyl)-acetamide (7)

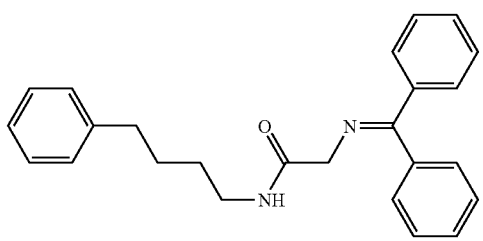

Phenylbutylamine (8.2 g, 52 mmol) is added to a mixture of BOC-Gly-PNB (14.82 g, 50 mmol) in dioxane (60 mL) and 1 M $K_2CO_3$ (60 mL). The mixture is stirred 16 h and then diluted with $CH_2Cl_2$ and washed with a saturated $NaHCO_3$ solution until the organic phase is colorless. The organics are dried ($MgSO_4$) and concentrated to provide [(4-phenyl-butylcarbamoyl)-methyl]-carbamic acid tert-butyl ester which is used as is without further purification.

The crude [(4-phenyl-butylcarbamoyl)-methyl]-carbamic acid tert-butyl ester is stirred in a solution of dioxane (150 mL) and HCl (4 M dioxane, 42 mL, 168 mmol) for 17 h. The volatiles are removed in vacuo to provide 2-amino-N-(4-phenyl-butyl)-acetamide, hydrogen chloride salt which is used as is without further purification.

2-Amino-N-(4-phenyl-butyl)-acetamide-hydrogen chloride salt is stirred with benzophenone imine (12.6 mL, 75 mmol) in $CH_2Cl_2$ (200 mL) for 24 h. The organics are then washed with water, dried ($MgSO_4$), and concentrated to provide 2-(diphenylmethylenamino)-N-(4-phenyl-butyl)-acetamide (7) as a white solid which is used without further purification.

Example 5

Biological Assays

CDC25A Assay

1X Assay Buffer: 30 mM Tris, pH 8.5; 75 mM NaCl; 0.67 mM EDTA; 0.033% bovine serum albumin (BSA); and 10 mM DTT.

Fluorescein Diphosphate (FDP) substrate: 5 mg FDP is reconstituted in 890 µl 10 nM Tris, pH 7.0–8.0 to make 10 mM stock. Aliquot and freeze at −20° C. until use.

Stock is diluted to 200 µM working stock (50× dilution). The assay requires 10 µl FDP per well.

Human recombinant CDC25A: Human recombinant CDC25A is cloned, expressed and purified. In the absence of well-characterized specific protein concentration or active site calculations, enzyme content is normalized across lots according to enzyme activity. The enzyme activity is linear over the duration of the assay, and the total relative fluorescence units (RFUs) generated should not exceed 10% of theoretical maximum. At 20 µM FDP in the assay, the signal should not exceed 25,000 RFUs over the duration of the assay.

Procedure: Polypropylene assay plates are labeled accordingly. 25 µl 100 µM test compound is added to the corresponding well of the assay plate. 55 µl of assay buffer is then added to each well, followed by 10 µl 200 µM FDP. The reaction is then initiated with the addition of 10 µl of 10×CDC25A. The cells are incubated for an hour and the reaction is subsequently terminated by addition of 10 µl stop solution (0.5 M NaOH/50% ethanol). Fluorescence is read at ex485/em538/cutoff 530.

PTP1B Assay

1× Assay Buffer: 50 mM ADA (N-[2-Acetamido]-2-iminodiacetic acid; N-[Carbamoylmethyl]iminodiacetic acid), pH 6.0; 1 mM EDTA; 10 mM DTT; 0.1% TritonX.

Fluorescein Diphosphate (FDP) substrate: 5 mg FDP is reconstituted in 890 µl 10 mM Tris, pH 7.0–8.0 to make 10 mM stock. Aliquot and freeze at −20° C. until use.

Stock is diluted to 200 µM working stock in assay buffer (50X dilution). The assay requires 10 µl FDP per well.

Human recombinant PTP1B: Human recombinant PTP1B is cloned, expressed, and purified. In the absence of well-characterized specific protein concentration or active site calculations, enzyme content is normalized across lots according to enzyme activity. The enzyme activity is linear over the duration of the assay, and the total relative fluorescence units (RFUs) generated should not exceed 10% of theoretical maximum. At 20 µM FDP in the assay, the signal should not exceed 11,000 RFUs over the duration of the assay. Quantum yield (fluorescence per unit fluorophore) is decreased at pH 6.0.

Procedure: Polypropylene assay plates are labeled accordingly. 25 µl 100 µM test compound is added to the corresponding well of the assay plate. 55 µl of assay buffer is then added to each well, followed by 10 µl 200 µM FDP. The reaction is then initiated with the addition of 10 µl of 10X PTB1B. The cells are incubated for 30 minutes and the reaction is subsequently terminated by addition of 10 µl stop solution (0.5 M NaOH/50% ethanol). Fluorescence is read at ex485/em538/cutoff 530.

The compounds of the present invention are tested for their activity in the CDC25A and PTP-1B enzymes according to the procedures described above. The results are measured as Ki values (µM) in both assays and range from about between 0.01 µM to 1000 µM.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula

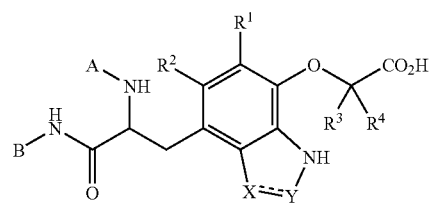

and pharmaceutically acceptable salts and prodrugs thereof, wherein

---- is an optional bond;

$R^1$ and $R^2$ are independently selected from hydrogen, hydroxy, halogen, lower alkyl, lower alkoxy, alkoxyalkyl, hydroxyalkyl, lower alkenyl, amino, mono- or dialkylamino, cyano, nitro, trifluromethyl, —CON($^6$)$_2$ or —COOR$^6$;

$R^3$ and $R^4$ are independently selected from hydrogen, halogen, lower alkyl, lower alkenyl, cycloalkyl, cyano, —CON(R$^6$)$_2$ or —COOR$^6$;

A is selected from lower alkyl, lower alkenyl, lower alkynyl, —C(O)R$^7$, —S(O)$_2$R$^7$, —C(O)NHR$^7$, —CO$_2$R$^7$, —(CH$_2$)$_n$S(O)$_q$R$^7$, —(CH$_2$)$_p$C(O)R$^7$, —(CH$_2$)$_p$C(O)NHR$^7$, —(CH$_2$)$_p$CO$_2$R$^7$, (CH$_2$)$_n$OR$^7$, or aryl, heteroaryl, arylalkyl or heteroarylalkyl, where the ring portion of each is optionally substituted with one, two or three groups independently selected from halogen, lower alkyl, hydroxy, amino, mono- or dialkylamino, trifluoromethyl, —C(O)R$^8$, —COOR$^8$, —C(O)NHR$^8$ or —OR$^8$;

B is selected from hydrogen, lower alkyl, lower alkenyl, lower alkynyl, —(CH$_2$)$_n$S(O)$_q$R$^7$, —(CH$_2$)$_p$C(O)R$^7$, —(CH$_2$)$_p$C(O)NHR$^7$, —(CH$_2$)$_p$CO$_2$R$^7$, (CH$_2$)$_n$OR$^7$, or aryl, heteroaryl, arylalkyl, arylalkenyl, arylalkynyl, heteroarylalkyl, heteroarylalkenyl or heteroarylalkynyl, where the ring portion of each is optionally substituted with one, two or three groups independently selected from halogen, lower alkyl, hydroxy, amino, mono- or dialkylamino, trifluoromethyl, —C(O)R$^8$, —COOR$^8$, —C(O)NHR$^8$ or —OR$^8$;

n is 2–4;
p is 1–2;
q is 0–2;

$R^6$ is selected from hydrogen, lower alkyl, or lower alkenyl;

$R^7$ is selected from aryl, heteroaryl, arylalkyl, or heteroarylalkyl, where the ring portion of each is optionally substituted with one, two or three groups independently selected from halogen, lower alkyl, hydroxy, amino, mono- or dialkylamino, trifluoromethyl, —C(O)R$^8$, —COOR$^8$, —C(O)NHR$^8$ or —OR$^8$;

$R^8$ is independently selected from hydrogen, or
lower alkyl, aryl or heteroaryl optionally substituted with one, two or three groups independently selected from lower alkyl, halogen, lower alkoxy, hydroxy, amino, mono- or dialkylamino, or trifluoromethyl;

X and Y are nitrogen or CR$^{10}$; and
$R^{10}$ is selected from hydrogen, hydroxy, halogen or amino.

2. A compound according to claim 1 having the formula

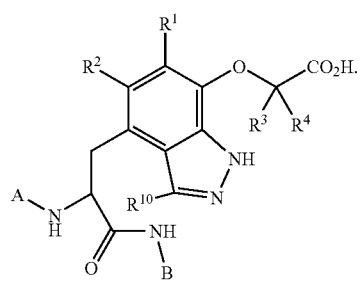

3. A compound according to claim 1 having the formula

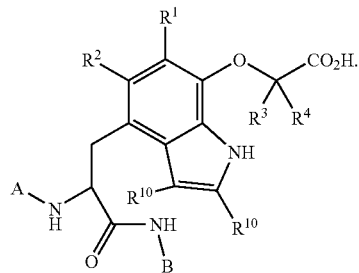

4. A compound according to claim 1 having the formula

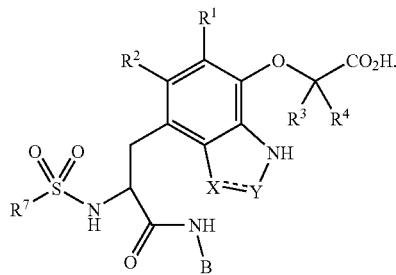

5. A compound according to claim 1 wherein the fused-ring system forms groups selected from indole, indazole, indoline, benzotriazole or benzoimidazole, each of which may be optionally substituted with one, two or three groups selected from —OH, halogen, amino, lower alkyl or oxo.

6. A compound according to claim 5 wherein the fused-ring system forms groups selected from indole or indazole, each of which may be optionally substituted with one, two or three groups selected from —OH, halogen, amino, lower alkyl or oxo.

7. A compound according to claim 2 wherein
$R^1$ is selected from hydrogen, halogen and methyl;
$R^2$ is selected from hydrogen and halogen;
$R^3$ is selected from hydrogen and fluorine;
$R^4$ is hydrogen;
A is —C(O)R$^7$ or —S(O)$_2$R$^7$;
B is selected from lower alkyl, aryl-C$_{2-6}$-alkyl, 5–6-membered heteroaryl-C$_{2-6}$-alkyl, and (CH$_2$)$_n$OR$^7$;
$R^7$ is aryl, 5–6membered heteroaryl, aryl-C$_{1-3}$-alkyl, heteroaryl-C$_{1-3}$-alkyl; and
n is 2–4.

8. A compound according to claim 3 wherein
$R^1$ is selected from hydrogen, halogen and methyl;
$R^2$ is selected from hydrogen and halogen;
$R^3$ is selected from hydrogen and fluorine;
$R^4$ is hydrogen;
A is —C(O)R$^7$ or —S(O)$_2$R$^7$;
B is selected from lower alkyl, aryl-C$_{2-6}$-alkyl, 5–6-membered heteroaryl-C$_{2-6}$-alkyl, and (CH$_2$)$_n$OR$^7$;
$R^7$ is aryl, 5–6 membered heteroaryl, aryl-C$_{1-3}$-alkyl, heteroaryl-C$_{1-3}$-alkyl;
each $R^{10}$ is independently hydrogen or a halogen;
and n is 2–4.

9. A compound according to claim 4 wherein
the optional bond - - - is present;
$R^1$ is selected from hydrogen, halogen and methyl;
$R^2$ is selected from hydrogen and halogen;

$R^3$ is selected from hydrogen and fluorine;
$R^4$ is hydrogen;
B is selected from lower alkyl, aryl-$C_{2-4}$-alkyl 5–6-membered heteroaryl-$C_{2-6}$-alkyl, or $(CH_2)_nOR^7$;
$R^7$ is aryl, 5–6 membered heteroaryl, aryl-$C_{1-3}$-alkyl or heteroaryl-$C_{1-3}$-alkyl;
X is —$CR^{10}$, wherein $R^{10}$ is hydrogen or halogen;
Y is nitrogen or —$CR^{10}$, wherein $R^{10}$ is hydrogen;
and n is 2–4.

10. A compound according to claim 1 which is
{4-[2-Benzenesulfonylamino-2-(4-phenyl-butylcarbamoyl)-ethyl]-1H-indazol-7-yloxy}-acetic acid;
{4-[2-Benzenesulfonylamino-2-(4-phenyl-butylcarbamoyl)-ethyl]-6-chloro-1H-indazol-7-yloxy}-fluoro-acetic acid;
{4-[2-Benzenesulfonylamino-2-(4-phenyl-butylcarbamoyl)-ethyl]-1H-indazol-7-yloxy}-fluoro-acetic acid;
{4-[2-Benzenesulfonylamino-2-(4-phenyl-butylcarbamoyl)-ethyl]-1H-indol-7-yloxy}-fluoro-acetic acid, sodium salt;
{4-[2-Benzenesulfonylamino-2-(4-phenyl-butylcarbamoyl)-ethyl]-1H-indol-7-yloxy}-acetic acid; and
{4-[2-Benzenesulfonylamino-2-(4-phenyl-butylcarbamoyl)-ethyl]-3-bromo-1H-indol-7-yloxy}-acetic acid.

11. A pharmaceutical formulation comprising a compound according to claim 1 and a pharmaceutically acceptable carrier.

12. A method of treating Type II Diabetes Mellitus in a patient in need thereof comprising administering to the patient a therapeutically effective amount of the compound according to claim 1.

13. A method of inhibiting tyrosine phosphatase activity in a mammal for the treatment of Type II Diabetes Mellitus, comprising administration of an effective amount of a compound of claim 1 to said mammal.

14. A method of inhibiting PTP-1B activity in a mammal for the treatment of Type II Diabetes Mellitus, comprising administration of an effective amount of a compound of claim 1 to said mammal.

15. A method of inhibiting CDC25A activity in a mammal for the treatment of Type II Diabetes Mellitus, comprising administration of an effective amount of a compound of claim 1 to said mammal.

* * * * *